(12) United States Patent
Heine et al.

(10) Patent No.: US 7,852,616 B2
(45) Date of Patent: Dec. 14, 2010

(54) POWER SOURCE FOR DIAGNOSTIC INSTRUMENTS

(75) Inventors: Helmut Heine, Diessen (DE); Oliver Heine, Herrsching (DE); Dirk Schade, Penzberg (DE); Elsa Ploetz, Andechs (DE); Stefan Knesewitsch, Herrsching (DE); Norbert Merkt, Breitbrunn (DE); Sebastian Duy, Otterfing (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 1155 days.

(21) Appl. No.: 11/504,655

(22) Filed: Aug. 16, 2006

(65) Prior Publication Data

US 2007/0069713 A1     Mar. 29, 2007

(30) Foreign Application Priority Data

Aug. 18, 2005   (DE) .................. 20 2005 013 062 U

(51) Int. Cl.
*H02B 1/00* (2006.01)
(52) U.S. Cl. ...................... 361/601; 361/616
(58) Field of Classification Search ................. 361/600, 361/601, 615, 616, 640, 829, 837; 307/139, 307/142; 606/2
See application file for complete search history.

(56) References Cited

U.S. PATENT DOCUMENTS

| 6,342,766 B1 * | 1/2002 | Cook et al. .................... 315/32 |
| 6,376,770 B1 * | 4/2002 | Hyde .......................... 174/58 |
| 6,443,322 B1 * | 9/2002 | Braun et al. ................ 220/4.02 |
| 6,816,359 B1 * | 11/2004 | Hsiao ......................... 361/601 |
| 7,397,654 B2 * | 7/2008 | Mori ..................... 361/679.01 |

* cited by examiner

*Primary Examiner*—Thuy Vinh Tran
(74) *Attorney, Agent, or Firm*—Rothwell, Figg, Ernst & Manbeck, P.C.

(57) ABSTRACT

A power source device for diagnostic instruments is adapted for a connection of different types of illuminating devices and includes an active control unit for controlling an operating state of a power source in dependence on a type of a connected one of the illuminating devices.

7 Claims, 2 Drawing Sheets

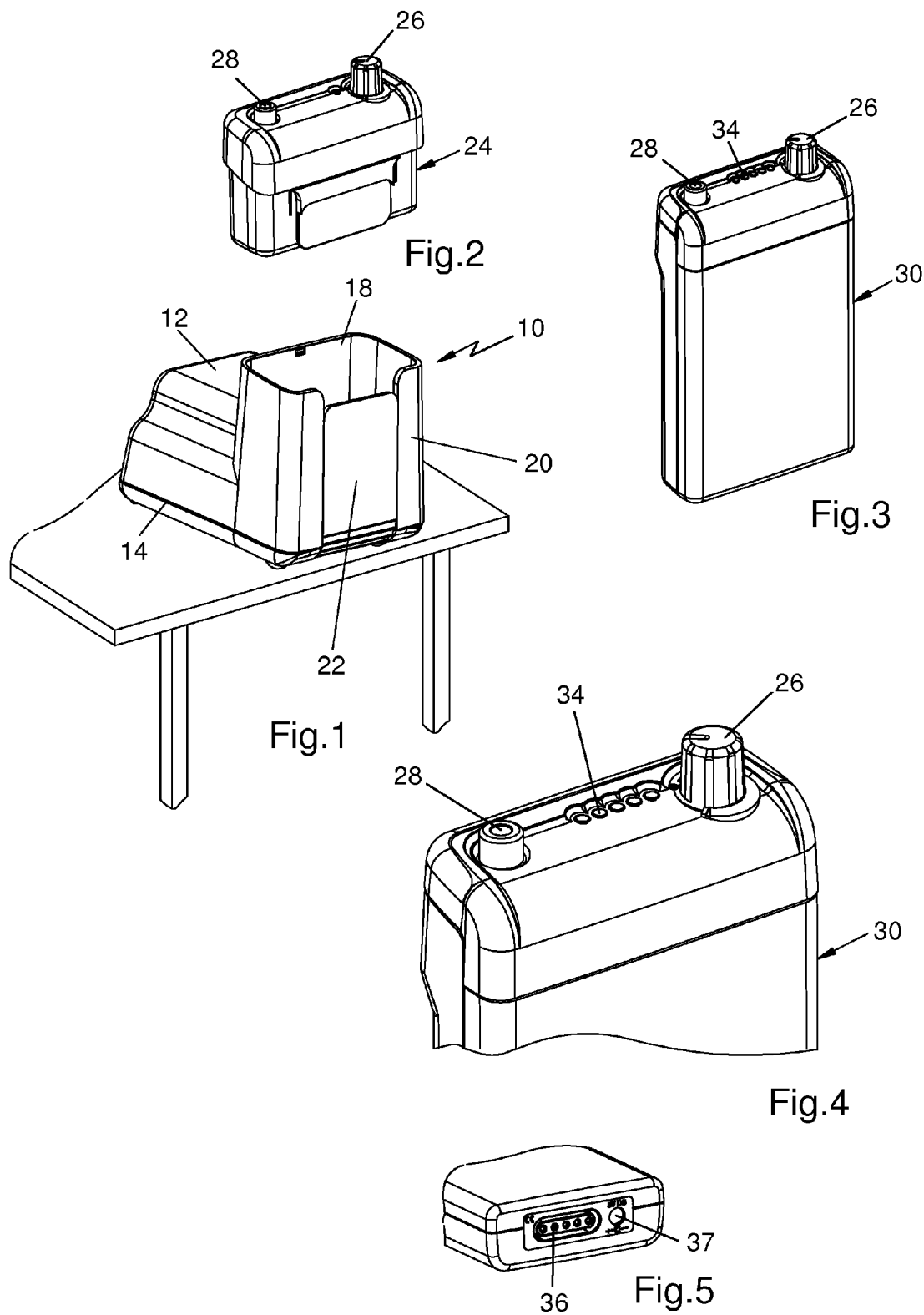

POWER SOURCE FOR DIAGNOSTIC INSTRUMENTS

BACKGROUND OF THE INVENTION

1. Field of the Invention

Figure 6:
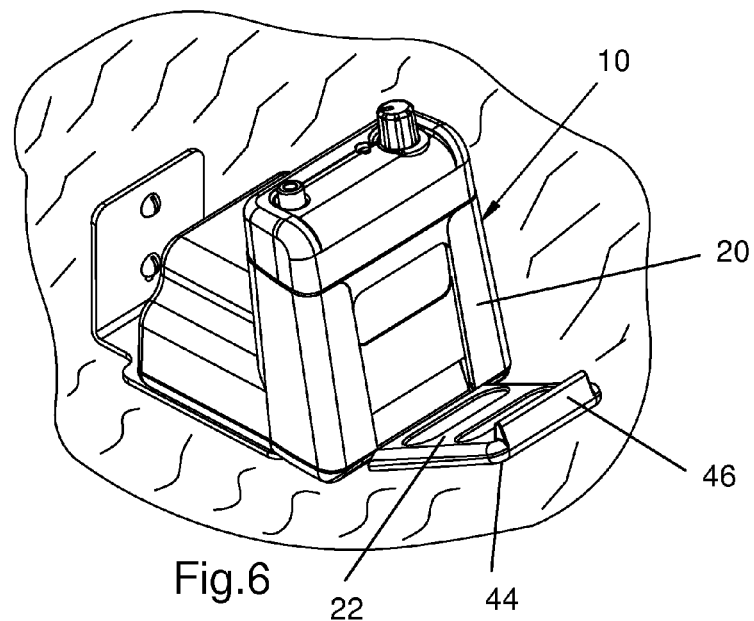

The invention refers to a power source device for a connection of different types of illuminating means.

2. Description of the Background Art

In the medical field, special illuminating means optimized towards the specific application in each case (e.g. bowl reflector lamps and ophthalmoscopes) are used for diagnostic purposes and general examinations. As the light source for these, incandescent bulbs or light emitting diodes (LEDs) are used. Controlling the brightness of these light sources requires a control arrangement which is effected either at the power source itself or via a controller provided externally. In the case of bowl reflector lamps and ophthalmoscopes, such an external controller is normally mounted for ergonomic reasons on a head support frame on which the illuminating device is also mounted. As power source, either line-connected stationary power sources or mobile power sources with rechargeable batteries are known. There are stationary power sources which are deposited on a work surface. Other stationary power sources are constructed for mounting on a wall. In the case of wall mounting, a hanger is usually integrated in the power source mounted on the wall, on which the illuminating device can be hung up when it is not used. In this arrangement, the hanger is usually used as a switch which can switch the operating power on and off. Mobile power sources are usually charged up via a separate charger.

The power sources currently known are equipped either specially for supplying power to LEDs or supplying power to incandescent bulbs. Each of these light sources requires its own power source.

SUMMARY OF THE INVENTION

The object of the invention is to provide a power source device for diagnostic instruments with a wide range of uses.

This object is achieved by a power source device for a connection of different types of illuminating means, comprising an active control unit for controlling an operating state of a power source in dependence on a type of a connected one of said illuminating means.

The power source device according to the invention is equipped with an active control unit which controls the operating state of the power source, e.g. the output voltage, status indications or operating functions in dependence on the type of illuminating means connected. LEDs and incandescent bulbs have different electrical characteristics and must be operated with different output voltages by the power source. As a rule, the brightness of incandescent bulbs is controlled by the voltage, whereas LEDs are controlled via the current. In the case of LEDs the current must be stable. A threshold voltage must be exceeded.

The power source device according to the invention saves the user from having to set the correct output voltage on the power source but it can automatically detect the connected type of light source. This is necessary, in particular, when a manufacturer's illuminating means which are already on the market needs a special form and amplitude of the input voltage. The power source which independently detects the light source connected is capable of providing another specific output voltage. The operation with LED is preferably effected by means of direct voltage whereas incandescent lamps are operated with pulse-width modulation.

The power source according to the invention is also mechanically compatible with illuminating means already on the market. For this purpose, plug-in contacts and possibly two-wire feed lines must also advantageously be taken into consideration in addition to special requirements for the output voltage.

In a preferred embodiment, the user can adjust the brightness on an external controller. In this case, a controller power source is deactivated in order to ensure unambiguous and intuitive operation via the external control. Such an external controller is provided, for example, on the headband of a bowl reflector lamp or of an ophthalmoscope since this is ergonomically advantageous.

A preferred power source device of the invention comprises comprising a basic module having a bottom area which is constructed in such a manner that said basic module can be deposited on a plane surface. In said basic module, a bay opening upwardly is provided for receiving a power source, connecting means for a plug-in connection of said power source to a power supply being provided at a bottom of said bay. At an front face of said basic module, a flap element is supported such that it can swivel about a horizontal swiveling axis from a closed position in which said flap element rests against said front face into a suspended position in which one end of said flap element protrudes from said front face, wherein a switch element is provided adjoining an other end of said flap element, said switch element interrupting a connection between said power source and a connected load when a pressure is exerted from above onto said flap element located in said suspended position.

The power source device according to the invention can be used as a stationary power source with power line supply as a floor unit or as a wall unit which can be mounted on the wall. A second, mobile and battery-operated power source can be used in mobile operation. The rechargeable batteries are charged up by means of a separate power line transformer.

When the power source device according to the invention is provided with a stationary power source, it can be retrofitted with the mobile power source which can be inserted into the same bay of the housing as the stationary power source.

For wall mounting, the flap element can be opened and, as a result, forms a switch which switches off the operating power when a pressure is exerted from above on the flap element as is the case, for example, when a bowl reflector lamp is hung up on the flap element.

The power source device according to the invention can be used in a very flexible manner. The user can use the power source device in a stationary or mobile manner as a floor unit or as a wall unit as desired.

BRIEF DESCRIPTION OF THE INVENTION

Figure 8:
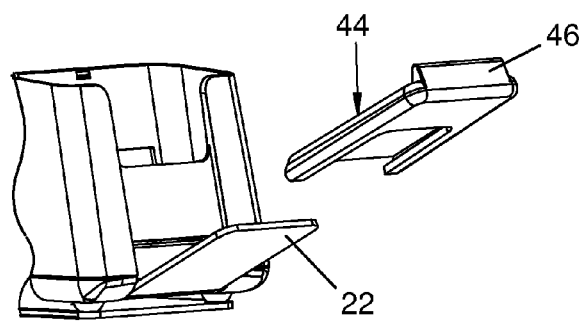
Figure 7:
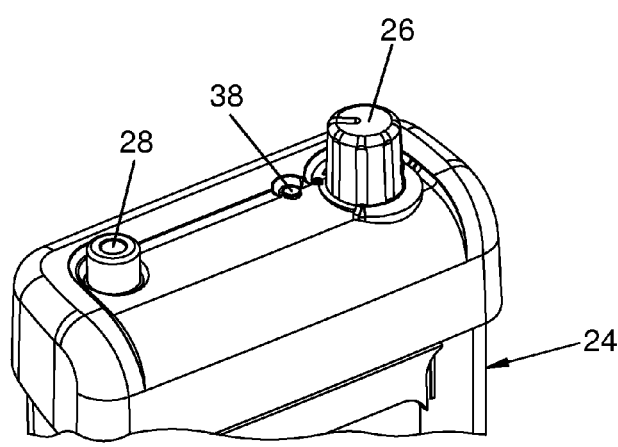

In the text which follows, an exemplary embodiment of the invention is explained in greater detail with reference to drawings, in which:

FIG. 1 shows a basic module of a power source device deposited on a work surface, FIG. 2 shows a stationary power source for insertion into the basic module of FIG. 1, FIG. 3 shows a mobile power source for insertion into the basic module of FIG. 1, FIG. 4 shows an enlarged view of the section of the mobile power source of FIG. 3, FIG. 5 shows a view of the bottom of the mobile power source of FIG. 3, FIG. 6 shows the basic module of FIG. 1, mounted on a wall, the stationary power source being inserted, FIG. 7 shows an enlarged view of the top section of the stationary power source, FIG. 8 shows how a holding element is placed onto a flap element of the basic module.

DETAILED DESCRIPTION OF THE INVENTION

The basic module 10 shown in FIG. 1 has a housing section 12 in which electronics for connection to a power line supply are accommodated. The housing section 12 is adjoined by a bay 18 into which a stationary power source 24 (FIG. 2) or a mobile power source 30 (FIG. 3) can be inserted from above. On the underside of the power source 30, terminals 36 (FIG. 5) are provided which can be stuck onto corresponding terminals on the bottom of the bay 18 in order to establish a connection of the power source 30 for supplying the charging power. In addition, a socket 37 is provided for connecting a plug-in transformer if the power source 30 is not used together with the basic module 10.

The housing section 12 and the bay 18 extend towards the top from a level bottom area 14. On the front end face 20 of the bay 18, a flap element 22 can be swiveled towards the bottom about a horizontal axis from the closed position shown in FIG. 1, in which it is flush with the end face 20, into the suspended position shown in FIG. 6 about a horizontal swiveling axis, which adjoins the bottom area 14. When the flap element 22 is in the suspended position shown in FIG. 6, a holding element 44 can be pushed onto the flap element (see FIG. 8), which has at its outer end facing away from the end face 20 a holding projection 46 extending towards the top. The holding projection 46 prevents a device suspended on the flap element 22, such as, for example, a head band, from slipping away.

At the end of the flap element 22 located adjoining the end face 20, a switching element (not shown) is provided which interrupts the connection between the respective power source 24 and 30, and a connected load when a pressure is exerted from the top onto the flap element 22 located in the suspended position.

As can be seen in FIG. 7, a connection 28 for a power supply for an illuminating device and a rotatable control knob 26 of a control device (not shown) for the brightness of an illuminating device is provided on the top of the stationary power source 24. In addition, there is an operating status indicator 38. Instead of the operating status indicator 38, the mobile power source 30 has a number of charge control lamps 34.

Inside the power sources 24 and 30, respectively, active control electronics are provided which can remotely control the operating state of the power source 24 and 30, respectively, including the output voltage, status indicators and operating functions, inter alia. The control signals can be wirelessly transmitted from the control unit. It is also possible to transmit the control signals via an additional control line or via the same feed line by means of which the operating power is transmitted.

The control knob 26 is connected to a control device (not shown) which controls the current for adjusting the brightness in a LED. During operation with an incandescent lamp, control is effected by adjusting the output voltage.

In a preferred embodiment, the control device has two operating states. In the first operating state for controlling the brightness of an incandescent lamp, the control device is active on the respective power source and the output signal of the power source can be controlled (duty ratio of the PWM signal). In the second operating state, the controller on the power source is deactivated. The output signal on the power source can then no longer be controlled. In the second operating state, control can be effected by an external controller which can be mounted, for example, on a headband on which an illuminating device with LED is mounted.

The first operating state is caused or determined when an incandescent lamp is used. When a LED is used, the second operating state is selected.

The invention claimed is:

1. A power source device comprising a basic module having a bottom area which is constructed in such a manner that said basic module can be deposited on a plane surface, wherein in said basic module, a bay opening upwardly is provided for receiving a power source, connecting element for a plug-in connection of said power source to a power supply being provided at a bottom of said bay opening, at a front face of said basic module, a flap element is supported such that it can swivel about a horizontal swiveling axis from a closed position in which said flap element rests against said front face into a suspended position in which one end of said flap element protrudes from said front face, wherein a switch element is provided adjoining an other end of said flap element, said switch element interrupting a connection between said power source and a connected load when a pressure is exerted from above onto said flap element located in said suspended position.

2. A power source device as claimed in claim 1, wherein the power source is a stationary power source or a mobile power source with rechargeable batteries accommodated in said bay.

3. A power source device as claimed in claim 1, for use with diagnostic instruments, wherein the power source device is is connected to different types of illuminating elements, the power source device further comprising an active control unit for controlling an operating state of a power source in dependence on a type of a connected one of said illuminating means.

4. A power source device as claimed in claim 3, wherein said connected one of said illuminating element comprises at least one LED or at least one incandescent bulb.

5. A power source device as claimed in claim 3, wherein control signals of said control unit can be are transmitted wirelessly to said power source.

6. A power source device as claimed in claim 3, further comprising a feed line for operating power to said connected one of said illuminating elements which is used for transmitting control signals at the same time.

7. A power source device as claimed in claim 3, further comprising a control device for controlling an output voltage.

* * * * *